United States Patent
Xie et al.

(10) Patent No.: US 9,700,878 B2
(45) Date of Patent: Jul. 11, 2017

(54) PROCESSES USING MOLECULAR SIEVE SSZ-98

(71) Applicants: Dan Xie, Richmond, CA (US); Stacey Ian Zones, San Francisco, CA (US); Christopher Michael Lew, Richmond, CA (US); Tracy Margaret Davis, Novato, CA (US)

(72) Inventors: Dan Xie, Richmond, CA (US); Stacey Ian Zones, San Francisco, CA (US); Christopher Michael Lew, Richmond, CA (US); Tracy Margaret Davis, Novato, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 188 days.

(21) Appl. No.: 14/790,921

(22) Filed: Jul. 2, 2015

(65) Prior Publication Data

US 2016/0001273 A1    Jan. 7, 2016

Related U.S. Application Data

(60) Provisional application No. 62/020,638, filed on Jul. 3, 2014.

(51) Int. Cl.
| | |
|---|---|
| *B01D 53/56* | (2006.01) |
| *B01J 29/56* | (2006.01) |
| *B01D 53/02* | (2006.01) |
| *B01D 53/94* | (2006.01) |
| *B01J 20/18* | (2006.01) |

(Continued)

(52) U.S. Cl.
CPC .............. *B01J 29/56* (2013.01); *B01D 53/02* (2013.01); *B01D 53/228* (2013.01); *B01D 53/9418* (2013.01); *B01D 53/9486* (2013.01); *B01J 20/18* (2013.01); *B01J 29/50* (2013.01); *B01J 29/54* (2013.01); *B01J 35/065* (2013.01); *C01B 39/305* (2013.01); *C07C 1/20* (2013.01); *C07C 209/00* (2013.01); *C07C 209/16* (2013.01); *B01D 2253/1085* (2013.01); *B01D 2255/50* (2013.01); *B01D 2258/012* (2013.01);

(Continued)

(58) Field of Classification Search
None
See application file for complete search history.

(56) References Cited

U.S. PATENT DOCUMENTS

| | | | |
|---|---|---|---|
| 2,942,932 | A | 6/1960 | Elliott |
| 2,950,952 | A | 8/1960 | Breck et al. |

(Continued)

FOREIGN PATENT DOCUMENTS

| | | | |
|---|---|---|---|
| WO | 03026775 | 4/2003 | |
| WO | WO 2010065319 A2 * | 6/2010 | ............ B01D 53/02 |
| WO | WO 2010088243 A2 * | 8/2010 | ............ B01D 53/02 |

OTHER PUBLICATIONS

PCT International Search Report, PCT/US2015/022185, mailed Jul. 15, 2015.

(Continued)

*Primary Examiner* — Anita Nassiri Motlagh
(74) *Attorney, Agent, or Firm* — Terrence M. Flaherty

(57) ABSTRACT

Uses for a new crystalline molecular sieve designated SSZ-98 are disclosed. SSZ-98 has the ERI framework type and is synthesized using a N,N'-dimethyl-1,4-diazabicyclo[2.2.2]octane dication as a structure directing agent.

15 Claims, 8 Drawing Sheets

(51) Int. Cl.

| | | |
|---|---|---|
| *B01J 29/50* | (2006.01) | |
| *B01J 29/54* | (2006.01) | |
| *C07C 1/20* | (2006.01) | |
| *C07C 209/16* | (2006.01) | |
| *B01D 53/22* | (2006.01) | |
| *C01B 39/30* | (2006.01) | |
| *C07C 209/00* | (2006.01) | |
| *B01J 35/06* | (2006.01) | |

(52) U.S. Cl.
CPC .......... *C07C 2529/70* (2013.01); *Y02P 20/52* (2015.11); *Y02P 30/42* (2015.11)

(56) References Cited

U.S. PATENT DOCUMENTS

| | | |
|---|---|---|
| 3,699,139 A | 10/1972 | Rubin et al. |
| 4,086,186 A | 4/1978 | Rubin et al. |
| 4,297,328 A | 10/1981 | Ritscher et al. |
| 4,503,023 A | 3/1985 | Breck et al. |
| 4,677,242 A | 6/1987 | Kaiser |
| 4,737,592 A | 4/1988 | Abrams et al. |
| 7,344,694 B2 | 3/2008 | Miller et al. |
| 2006/0073094 A1 | 4/2006 | Miller et al. |

OTHER PUBLICATIONS

J.H. Lee, M.B. Park, J.K. Lee, H-K. Min, M.K. Song and S.B. Hong "Synthesis and Characterization of ERI-Type UZM-12 Zeolites and Their Methanol-to-Olefin Performance" J. Am. Chem. Soc. 2010, 132, 12971-12982.

J.M. Bennett and J.A. Gard "Non-identity of the zeolites erionite and offretite" Nature, 1967, 214, 1005-1006.

K.P. Lillerud and J.H. Raeder "On the synthesis of erionite-offretite intergrowth zeolites" Zeolites, 1986, 6, 474-483.

M.L. Occelli, R.A. Innes, S.S. Pollack and J.V. Sanders "Quaternary ammonium cation effects on the crystallization of offretite-erionite type zeolites: Part 1. Synthesis and catalytic properties" Zeolites, 1987, 7, 265-271.

A. Alberti, A. Martucci, E. Galli and Vezzalini "A reexamination of the crystal structure of erionite" Zeolites, 1997, 19, 349-352.

* cited by examiner

PROCESSES USING MOLECULAR SIEVE SSZ-98

CROSS-REFERENCE TO RELATED APPLICATIONS

This application claims the priority benefit of U.S. Provisional Application No. 62/020,638, filed Jul. 3, 2014, which is incorporated herein by reference.

TECHNICAL FIELD

This disclosure relates to new crystalline molecular sieve designated SSZ-98, a method for preparing SSZ-98 using a N,N'-dimethyl-1,4-diazabicyclo[2.2.2]octane dication as a structure directing agent ("SDA"), and uses for SSZ-98. These materials have the ERI framework type. The method enables control over silica-to-alumina ratio, crystal size, and morphology of these materials.

BACKGROUND

Molecular sieves are a commercially important class of crystalline materials. They have distinct crystal structures with ordered pore structures which are demonstrated by distinct X-ray diffraction patterns. The crystal structure defines cavities and pores which are characteristic of the different species.

Molecular sieves are classified by the Structure Commission of the International Zeolite Association (IZA) according to the rules of the IUPAC Commission on Zeolite Nomenclature. According to this classification, framework type zeolites and other crystalline microporous molecular sieves, for which a structure has been established, are assigned a three letter code and are described in the "*Atlas of Zeolite Framework Types*," Sixth Revised Edition, Elsevier (2007).

ERI framework type materials are characterized by three-dimensional 8-membered-ring pore/channel systems containing double-six-rings (d6R) and cages. Small pore molecular sieves containing d6R building units and cages have shown utility in methanol-to-olefins catalysis and in the selective catalytic reduction of nitrogen oxides ($NO_x$) to name some of the more important commercial applications.

ERI framework type molecular sieves are often intergrown with offretite (OFF) framework type molecular sieves, a topologically related molecular sieve. Intergrown ERI/OFF molecular sieves comprise regions of ERI framework type sequences and regions of OFF framework type sequences. There are number of references which disclose materials that are intergrowths of ERI and OFF. Zeolite T is disclosed in U.S. Pat. No. 2,950,952 and later discovered to be an ERI/OFF intergrowth (see J. M. Bennett et al., *Nature*, 1967, 214, 1005-1006). U.S. Pat. No. 3,699,139 discloses the use of a benzyltrimethylammonium cation to synthesize ERI/OFF intergrowth molecular sieves. U.S. Pat. No. 4,086,186 discloses using choline to synthesize ZSM-34 (an intergrowth). U.S. Pat. No. 4,503,023 discloses molecular sieves designated LZ-220 which are more siliceous forms of the known mineral erionite and its synthetic analog, zeolite T. M. L. Occelli et al. (*Zeolites*, 1987, 7, 265-271) disclose using templates designated DABCO(I) and DABCO(II) to synthesize ERI/OFF intergrowth molecular sieves.

U.S. Pat. No. 7,344,694 reports synthesizing an essentially pure ERI framework type molecular sieve designated UZM-12. UZM-12 is purported to have a Si/Al ratio of greater than 5.5. UZM-12 can be prepared as nanocrystallites having an average particle size of about 15 to about 50 nm and a spheroidal morphology. UZM-12 is synthesized via a charge-density mismatch approach whereby quaternary ammonium hydroxides are employed to solubilize aluminosilicate species, while crystallization inducing agents such as alkali and alkaline earth metals and more highly charged organoammonium cations are often introduced in a separate step.

SUMMARY

The present disclosure is directed to a new family of crystalline molecular sieves with unique properties, referred to herein as "molecular sieve SSZ-98" or simply "SSZ-98." SSZ-98 has the framework type designated "ERI" by the IZA.

In one aspect there is provided a crystalline ERI framework type molecular sieve having a $SiO_2/Al_2O_3$ mole ratio of from 15 to 50. The molecular sieve has either a rod-like crystal morphology or a plate crystal morphology. The SSZ-98 molecular sieve has, in its as-synthesized form, the X-ray diffraction lines of Table 3.

In another aspect, there is provided a method for preparing an ERI framework type molecular sieve by contacting under crystallization conditions: (1) at least one source of silicon oxide; (2) at least one source of aluminum oxide; (3) one or more sources of one or more elements selected from Groups 1 and 2 of the Periodic Table; (4) hydroxide ions; (5) a N,N'-dimethyl-1,4-diazabicyclo[2.2.2]octane dication; and (6) optionally, 18-crown-6.

There is also provided a process for preparing a crystalline molecular sieve by: (a) preparing a reaction mixture containing: (1) at least one source of silicon oxide; (2) at least one source of aluminum oxide; (3) one or more sources of one or more elements selected from Groups 1 and 2 of the Periodic Table; (4) hydroxide ions; (5) a N,N'-dimethyl-1, 4-diazabicyclo[2.2.2]octane dication; (6) optionally, 18-crown-6; and (7) water; and (b) subjecting the reaction mixture to crystallization conditions sufficient to form crystals of the molecular sieve. The present disclosure includes such a method wherein the crystalline molecular sieve has the ERI framework type and wherein the molecular sieve has, in its calcined form, the X-ray diffraction lines of Table 4.

The present disclosure further provides processes using SSZ-98. SSZ-98 has a composition, as-synthesized and in its anhydrous state, in terms of mole ratios as follows:

|  | Broad | Exemplary |
|---|---|---|
| $SiO_2/Al_2O_3$ | 15 to 50 | 20 to 40 |
| $(Q + A)/SiO_2$ | 0.01 to 0.10 | 0.01 to 0.10 |
| $M/SiO_2$ | 0.01 to 0.20 | 0.01 to 0.20 | wherein (1) Q is a N,N'-dimethyl-1,4-diazabicyclo[2.2.2] octane dication, and Q>0; (2) A is 18-crown-6, and A≥0; and (3) M is selected from the group consisting of elements from Groups 1 and 2 of the Periodic Table.

DETAILED DESCRIPTION

Introduction

Figure 1:
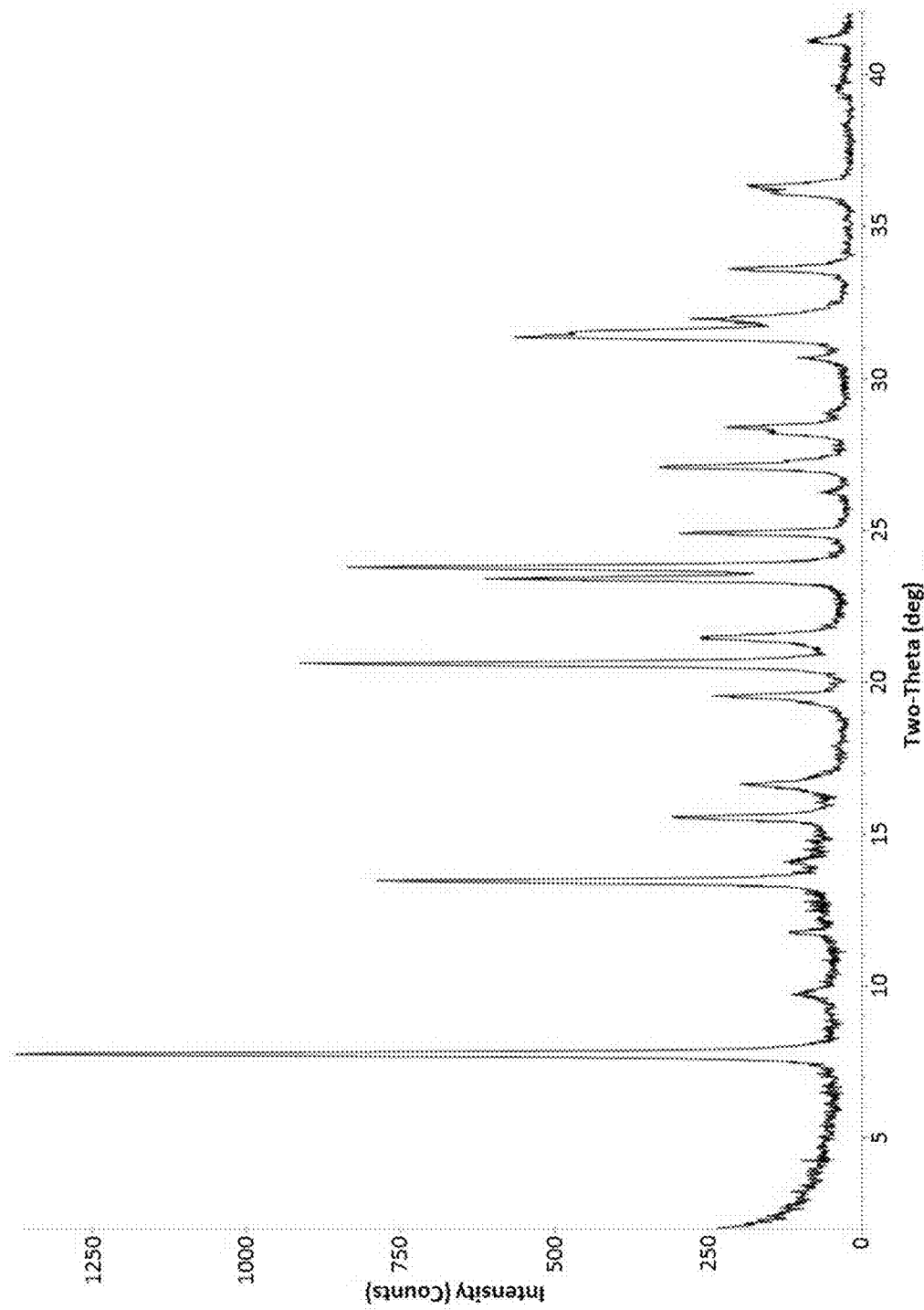
FIG. 1 is a powder X-ray diffraction (XRD) pattern of the as-synthesized molecular sieve prepared in Example 1.

The following terms will be used throughout the specification and will have the following meanings unless otherwise indicated.

The term "framework type" is used in the sense described in the "*Atlas of Zeolite Framework Types*," Sixth Revised Edition, Elsevier (2007).

As used herein, the numbering scheme for the Periodic Table Groups is as disclosed in *Chem. Eng. News*, 63(5), 27 (1985).

In preparing SSZ-98, a N,N'-dimethyl-1,4-diazabicyclo [2.2.2]octane dication ("dimethyl DABCO dication") is used, either alone or in combination with 18-crown-6 (designated compositional variable "A" herein), as an organic structure directing agent ("SDA"). The SDAs useful for making the molecular sieve are represented by the following structures (1) and (2), respectively:

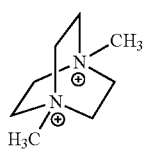

(1)

N,N'-dimethyl-1,4-diazabicyclo[2.2.2]octane dication

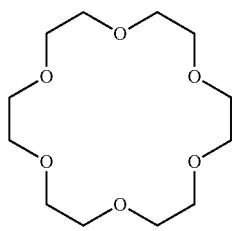

(2)

18-crown-6

The dimethyl DABCO dication is associated with anions which can be any anion that is not detrimental to the formation of the molecular sieve. Representative anions include elements from Group 17 of the Periodic Table (e.g., fluoride, chloride, bromide and iodide), hydroxide, acetate, sulfate, tetrafluoroborate, carboxylate, and the like.

Reaction Mixture

In general, the molecular sieve is prepared by: (a) preparing a reaction mixture containing (1) at least one source of silicon oxide; (2) at least one source of aluminum oxide; (3) one or more sources of one or more elements selected from Groups 1 and 2 of the Periodic Table; (4) hydroxide ions; (5) a N,N'-dimethyl-1,4-diazabicyclo[2.2.2]octane dication; (6) optionally, 18-crown-6; and (7) water; and (b) subjecting the reaction mixture to crystallization conditions sufficient to form crystals of the molecular sieve.

The composition of the reaction mixture from which the molecular sieve is formed, in terms of mole ratios, is identified in Table 1 below:

TABLE 1

| Components | Broad | Exemplary |
|---|---|---|
| $SiO_2/Al_2O_3$ | 10 to 50 | 20 to 40 |
| $M/SiO_2$ | 0.01 to 1.0 | 0.1 to 0.6 |
| $(Q + A)/SiO_2$ | 0.05 to 0.5 | 0.1 to 0.5 |
| $OH/SiO_2$ | 0.1 to 1.0 | 0.2 to 0.7 |
| $H_2O/SiO_2$ | 10 to 50 | 10 to 25 | wherein (1) Q is a N,N'-dimethyl-1,4-diazabicyclo[2.2.2] octane dication, and Q>0; (2) A is 18-crown-6, and A≥0; and (3) M is selected from the group consisting of elements from Groups 1 and 2 of the Periodic Table In embodiments, the A/Q mole ratio of the reaction mixture is from 0 to 1 (e.g., from 0 to 0.5, from 0 to 0.35, from 0.01 to 1, from 0.01 to 0.5, or from 0.01 to 0.35).

Sources of silicon oxide useful herein include fumed silica, precipitated silicates, silica hydrogel, silicic acid, colloidal silica, tetra-alkyl orthosilicates (e.g., tetraethyl orthosilicate), and silica hydroxides.

Sources of aluminum oxide useful herein include aluminates, alumina, and aluminum compounds such as $AlCl_3$, $Al_2(SO_4)_3$, $Al(OH)_3$, kaolin clays, and other zeolites. Examples of the source of aluminum oxide include LZ-210 zeolite and Zeolyst International's CBV 720 (type of zeolite Y).

As described herein above, for each embodiment described herein, the reaction mixture can be formed using at least one source of one or more elements selected from Groups 1 and 2 of the Periodic Table (referred to herein as M). Any M-containing compound which is not detrimental to the crystallization process is suitable. Sources for such Groups 1 and 2 elements include oxides, hydroxides, nitrates, sulfates, halides, acetates, oxalates, and citrates thereof. In one embodiment, M is potassium. In another embodiment, M is a combination of potassium and strontium.

The reaction mixture can also comprise seed crystals having a framework type of ERI, KFI, or a combination thereof to facilitate the crystallization process. When seed crystals are present, the mole ratio of seed crystals/$SiO_2$ in the reaction mixture is from 0.001 to 0.1, e.g., from 0.01 to 0.05.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

In practice, the molecular sieve is prepared by: (a) preparing a reaction mixture as described herein above; and (b) subjecting the reaction mixture to crystallization conditions sufficient to form crystals of the molecular sieve.

The reaction mixture is maintained at an elevated temperature until the molecular sieve is formed. The hydrothermal crystallization is usually conducted under pressure, and usually in an autoclave so that the reaction mixture is subject to autogenous pressure, at a temperature between 125° C. and 200° C.

The reaction mixture can be subjected to mild stirring or agitation during the crystallization step. It will be understood by one skilled in the art that the crystallized molecular sieves described herein can contain impurities, such as amorphous materials, unit cells having framework topologies which do not coincide with the molecular sieve, and/or other impurities (e.g., organic hydrocarbons).

Once the molecular sieve has formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum.

The molecular sieve can be used as-synthesized, but typically will be thermally treated (calcined). The term "as-synthesized" refers to the molecular sieve in its form after crystallization, prior to removal of the organic matter. The organic matter can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the organic matter from the molecular sieve. The organic matter can also be removed by photolysis techniques (e.g., exposing the SDA-containing molecular sieve product to light or electromagnetic radiation that has a wavelength shorter than visible light under conditions sufficient to selectively remove the organic matter from the molecular sieve) as described in U.S. Pat. No. 6,960,327.

The molecular sieve can subsequently be calcined in steam, air or inert gas at temperatures ranging from 200° C. to 800° C. for periods of time ranging from 1 to 48 hours, or more. Usually, it is desirable to remove the extra-framework cation (e.g., $K^+$) by ion-exchange or other known method and replace it with hydrogen, ammonium, or any desired metal-ion.

Where the molecular sieve formed is an intermediate material, the target molecular sieve can be achieved using post-synthesis techniques to allow for the synthesis of a target molecular sieve material having a higher silica-to-alumina ratio from an intermediate material by acid leaching or other similar dealumination methods.

The molecular sieves made from the process of the present invention can be formed into a wide variety of physical shapes. Generally speaking, the molecular sieve can be in the form of a powder, a granule, or a molded product, such as an extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying, or dried or partially dried and then extruded.

The molecular sieve can be composited with other materials resistant to temperature and other conditions employed in organic conversion processes. Such matrix materials include active and inactive materials and synthetic or naturally occurring molecular sieves as well as inorganic materials such as clays, silica and metal oxides. Examples of such materials and the manner in which they can be used are disclosed in U.S. Pat. Nos. 4,910,006 and 5,316,753.

Characterization of the Molecular Sieve

Molecular sieves made by the process described herein have a composition, as-synthesized and in the anhydrous state, as described in Table 2 (in terms of mole ratios):

TABLE 2

|  | Broad | Exemplary |
|---|---|---|
| $SiO_2/Al_2O_3$ | 15 to 50 | 20 to 40 |
| $(Q + A)/SiO_2$ | 0.01 to 0.10 | 0.01 to 0.10 |
| $M/SiO_2$ | 0.01 to 0.20 | 0.01 to 0.20 | wherein compositional variables Q, A and M are as described herein above.

SSZ-98 has the ERI framework topology. It is characterized by its X-ray diffraction pattern. The X-ray diffraction pattern lines of Table 3 are representative of as-synthesized SSZ-98 made in accordance with this disclosure.

TABLE 3

Characteristic Peaks for As-Synthesized SSZ-98

| 2-Theta[a] | d-spacing (nm) | Relative Intensity[b] |
|---|---|---|
| 7.78 | 1.136 | VS |
| 9.74 | 0.907 | W |
| 11.79 | 0.750 | W |
| 13.46 | 0.657 | S |
| 14.10 | 0.627 | W |
| 15.53 | 0.570 | M |
| 16.62 | 0.533 | W |
| 19.51 | 0.455 | W |
| 20.56 | 0.432 | VS |
| 21.40 | 0.415 | M |
| 23.38 | 0.380 | S |
| 23.76 | 0.374 | VS |
| 24.88 | 0.358 | W |

[a] ±0.20
[b] The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The X-ray diffraction pattern lines of Table 4 are representative of calcined SSZ-98 made in accordance with this disclosure.

TABLE 4

Characteristic Peaks for Calcined SSZ-98

| 2-Theta[a] | d-spacing (nm) | Relative Intensity[b] |
|---|---|---|
| 7.76 | 1.138 | VS |
| 9.78 | 0.904 | W |
| 11.79 | 0.750 | W |
| 13.45 | 0.658 | VS |
| 14.07 | 0.629 | W |
| 15.51 | 0.571 | W |
| 16.61 | 0.533 | W |
| 19.50 | 0.455 | W |
| 20.54 | 0.432 | S |
| 21.39 | 0.415 | W |
| 23.37 | 0.380 | M |
| 23.73 | 0.375 | S |
| 24.92 | 0.357 | W |

[a] ±0.20
[b] The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The crystallized ERI framework type materials disclosed herein are preferably "substantially free of OFF framework type materials" as determined by X-ray diffraction. The term "substantially free of OFF framework type materials" as used herein means that the ERI framework type materials disclosed herein contain less than 2.5% OFF framework type character, e.g., less than 1% OFF framework type character, less than 0.5% OFF framework type character, or no measurable OFF framework type character.

Minor variations in the X-ray diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the X-ray diffraction pattern. Notwithstanding these minor perturbations, the basic crystal lattice structure remains unchanged.

The powder X-ray diffraction patterns presented herein were collected by standard techniques. The radiation was $CuK_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

Processes Using SSZ-98

SSZ-98 is useful as an adsorbent for gas separations. SSZ-98 can also be used as a catalyst for converting oxygenates (e.g., methanol) to olefins and for making small amines. SSZ-98 can be used to reduce oxides of nitrogen in a gas streams, such as automobile exhaust. SSZ-98 can also be used to as a cold start hydrocarbon trap in combustion engine pollution control systems. SSZ-98 is particularly useful for trapping $C_3$ fragments.

Gas Separation

SSZ-98 can be used to separate gases. For example, it can be used to separate carbon dioxide from natural gas. Typically, the molecular sieve is used as a component in a membrane that is used to separate the gases. Examples of such membranes are disclosed in U.S. Pat. No. 6,508,860.

Oxygenate Conversion

The disclosed herein comprises a process for catalytic conversion of a feedstock comprising one or more oxygenates comprising alcohols and ethers to a hydrocarbon product containing light olefins, i.e., $C_2$, $C_3$ and/or $C_4$ olefins. The feedstock is contacted with SSZ-98 at effective process conditions to produce light olefins. The term "oxygenate" as used herein designates compounds such as alcohols, ethers, and carbonyl compounds (e.g., aldehydes, ketones, carboxylic acids). The oxygenate can contain from 1 to 10 carbon atoms, e.g., from 1 to 4 carbon atoms. The representative oxygenates include lower straight chained branched alcohols, and their unsaturated counterparts. Particularly suitable oxygenate compounds are methanol, dimethyl ether, and mixtures thereof The process disclosed can be conducted in the presence of one or more diluents which can be present in the oxygenate feed in an amount of from 1 to 99 mole %, based on the total number of moles of all feed and diluent components. Diluents include helium, argon, nitrogen, carbon monoxide, carbon dioxide, hydrogen, water, paraffins, hydrocarbons (such as methane and the like), aromatic compounds, or mixtures thereof. U.S. Pat. Nos. 4,677,242; 4,861,938; and 4,677,242 emphasize the use of a diluent to maintain catalyst selectivity toward the production of light olefins, particularly ethylene.

The oxygenate conversion is desirably conducted in the vapor phase such that the oxygenate feedstock is contacted in a vapor phase in a reaction zone with SSZ-98 at effective process conditions to produce hydrocarbons, i.e., an effective temperature, pressure, WHSV and, optionally, an effective amount of diluent. The process is conducted for a period of time sufficient to produce the desired light olefins. In general, the residence time employed to produce the desired product can vary from seconds to a number of hours. It will be readily appreciated that the residence time will be determined to a significant extent by the reaction temperature, the molecular sieve catalyst, the WHSV, the phase (liquid or vapor) and process design characteristics. The oxygenate feedstock flow rate affects olefin production. Increasing the feedstock flow rate increases WHSV and enhances the formation of olefin production relative to paraffin production. However, the enhanced olefin production relative to paraffin production is offset by a diminished conversion of oxygenate to hydrocarbons.

Light olefin products will form, although not necessarily in optimum amounts, at a wide range of pressures, including but not limited to autogenous pressures and pressures in the range from 0.1 kPa to 10 MPa. Conveniently, the pressure can be in the range from 7 kPa to 5 MPa, e.g., from 50 kPa to 1 MPa. The foregoing pressures are exclusive of diluents, if any are present, and refer to the partial pressure of the feedstock as it relates to oxygenate compounds and/or mixtures thereof. Lower and upper extremes of pressure can adversely affect selectivity, conversion, coking rate, and/or reaction rate; however, light olefins such as ethylene and/or propylene still may form.

The temperature which can be employed in the oxygenate conversion process can vary over a wide range depending, at least in part, on the molecular sieve catalyst. In general, the process can be conducted at an effective temperature of from 200° C. to 700° C. At the lower ends of the temperature range, and thus generally at a lower rate of reaction, the formation of the desired light olefins can become low. At the upper ends of the range, the process cannot form an optimum amount of light olefins and catalyst deactivation can be rapid.

The molecular sieve catalyst can be incorporated into solid particles in which the catalyst is present in an amount effective to promote the desired conversion of oxygenates to light olefins. In one aspect, the solid particles comprise a catalytically effective amount of the catalyst and at least one matrix material selected from the group consisting of binder materials, filler materials and mixtures thereof to provide a desired property or properties, e.g., desired catalyst dilution, mechanical strength and the like to the solid particles. Such matrix materials are often, to some extent, porous in nature and can or cannot be effective to promote the desired reaction. Filler and binder materials include, for example, synthetic and naturally occurring substances such as metal oxides, clays, silicas, aluminas, silica-aluminas, silica-magnesias, silica-zirconias, silica-thorias and the like. If matrix materials are included in the catalyst composition, the molecular sieve desirably comprises from 1 to 99 wt. % (e.g., from 5 to 90 wt. % or from 10 to 80 wt. %) of the total composition.

Synthesis of Amines

SSZ-98 can be used in a catalyst to prepare methylamine or dimethylamine. Dimethylamine is generally prepared in industrial quantities by continuous reaction of methanol (and/or dimethyl ether) and ammonia in the presence of a silica-alumina catalyst. The reactants are typically combined in the vapor phase, at temperatures of from 300° C. to 500° C., and at elevated pressures. Such a process is disclosed in U.S. Pat. No. 4,737,592.

The catalyst is used in its acid form. Acid forms of molecular sieves can be prepared by a variety of techniques. Desirably, the molecular sieve used to prepare dimethylamine will be in the hydrogen form, or have an alkali or alkaline earth metal, such as Na, K, Rb, or Cs, ion-exchanged into it.

The process disclosed herein involves reacting methanol, dimethyl ether, or a mixture thereof and ammonia in amounts sufficient to provide a carbon/nitrogen (C/N) ratio of from 0.2 to 1.5, e.g., from 0.5 to 1.2. The reaction is conducted at a temperature of from 250° C. to 450° C., e.g., from 300° C. to 400° C. Reaction pressures can vary from 7 to 7000 kPa, e.g., from 70 to 3000 kPa. A methanol and/or dimethyl ether space time of from 0.01 to 80 $h^{-1}$ (e.g., from 0.10 to 1.5 $h^{-1}$) is typically used. This space time is calculated as the mass of catalyst divided by the mass flow rate of methanol/dimethyl ether introduced into the reactor.

Reduction of Oxides of Nitrogen ($NO_x$)

SSZ-98 can be used for the catalytic reduction of the oxides of nitrogen in a gas stream. Typically, the gas stream also contains oxygen, often a stoichiometric excess thereof. Also, the molecular sieve can contain a metal or metal ions within or on it which are capable of catalyzing the reduction of the nitrogen oxides. Examples of such metals or metal ions include lanthanum, chromium, manganese, iron, cobalt, rhodium, nickel, palladium, platinum, copper, zinc, and mixtures thereof.

One example of such a process for the catalytic reduction of oxides of nitrogen in the presence of a zeolite is disclosed in U.S. Pat. No. 4,297,328. There, the catalytic process is the combustion of carbon monoxide and hydrocarbons and the catalytic reduction of the oxides of nitrogen contained in a gas stream, such as the exhaust gas from an internal combustion engine. The zeolite used is metal ion-exchanged, doped or loaded sufficiently so as to provide an effective amount of catalytic copper metal or copper ions within or on the zeolite. In addition, the process is conducted in an excess of oxidant, e.g., oxygen.

Treatment of Engine Exhaust (Cold Start Emissions)

Gaseous waste products resulting from the combustion of hydrocarbon fuels, such as gasoline and fuel oils, comprise carbon monoxide, hydrocarbons and nitrogen oxides as products of combustion or incomplete combustion, and can pose a serious health problem with respect to pollution of the atmosphere. While exhaust gases from other carbonaceous fuel-burning sources, such as stationary engines, industrial furnaces, etc., contribute substantially to air pollution, the exhaust gases from automotive engines are a principal source of pollution. Because of these concerns, the U.S. Environmental Protection Agency has promulgated strict controls on the amounts of carbon monoxide, hydrocarbons and nitrogen oxides which automobiles can emit. The implementation of these controls has resulted in the use of catalytic converters to reduce the amount of pollutants emitted from automobiles.

In order to achieve the simultaneous conversion of carbon monoxide, hydrocarbon and nitrogen oxide pollutants, it has become the practice to employ catalysts in conjunction with air-to-fuel ratio control means which functions in response to a feedback signal from an oxygen sensor in the engine exhaust system. Although these three component control catalysts work quite well after they have reached operating temperature of about 300° C., at lower temperatures they are not able to convert substantial amounts of the pollutants. What this means is that when an engine and in particular an automobile engine is started up, the three component control catalyst is not able to convert the hydrocarbons and other pollutants to innocuous compounds.

Adsorbent beds have been used to adsorb the hydrocarbons during the cold start portion of the engine. Although the process typically will be used with hydrocarbon fuels, the present disclosure can also be used to treat exhaust streams from alcohol-fueled engines. The adsorbent bed is typically placed immediately before the catalyst. Thus, the exhaust stream is first flowed through the adsorbent bed and then through the catalyst. The adsorbent bed preferentially adsorbs hydrocarbons over water under the conditions present in the exhaust stream. After a certain amount of time, the adsorbent bed has reached a temperature (typically about 150° C.) at which the bed is no longer able to remove hydrocarbons from the exhaust stream. That is, hydrocarbons are actually desorbed from the adsorbent bed instead of being adsorbed. This regenerates the adsorbent bed so that it can adsorb hydrocarbons during a subsequent cold start. The use of adsorbent beds to minimize hydrocarbon emissions during a cold start engine operation is known in the art. See, for example, U.S. Pat. Nos. 2,942,932; 3,699,683; and 5,078,979.

As stated, this disclosure generally relates to a process for treating an engine exhaust stream and, in particular, to a process for minimizing emissions during the cold start operation of an engine. The engine consists of any internal or external combustion engine which generates an exhaust gas stream containing noxious components or pollutants including unburned or thermally degraded hydrocarbons or similar organics. Other noxious components usually present in the exhaust gas include nitrogen oxides and carbon monoxide. The engine can be fueled by a hydrocarbon fuel. As used herein, the term "hydrocarbon fuel" includes hydrocarbons, alcohols and mixtures thereof. Examples of hydrocarbons which can be used to fuel the engine are the mixtures of hydrocarbons which make up gasoline or diesel fuel. The alcohols which can be used to fuel engines include ethanol and methanol. Mixtures of alcohols and mixtures of alcohols and hydrocarbons can also be used. The engine can be a jet engine, gas turbine, internal combustion engine, such as an automobile, truck or bus engine, a diesel engine or the like. The process of this disclosure is particularly suited for an internal combustion engine mounted in an automobile.

When the engine is started up, it produces a relatively high concentration of hydrocarbons in the engine exhaust gas stream as well as other pollutants. Pollutants will be used herein to collectively refer to any unburned fuel components and combustion byproducts found in the exhaust stream. For example, when the fuel is a hydrocarbon fuel, hydrocarbons, nitrogen oxides, carbon monoxide and other combustion byproducts will be found in the engine exhaust gas stream. The temperature of this engine exhaust stream is relatively cool, generally below 500° C. and typically in the range of from 200° C. to 400° C. This engine exhaust stream has the above characteristics during the initial period of engine operation, typically for the first 30 to 120 seconds after startup of a cold engine. The engine exhaust stream will typically contain from 500 to 1000 ppm hydrocarbons by volume.

In one embodiment, the engine exhaust gas stream which is to be treated is flowed over a combination of molecular sieves which preferentially adsorbs the hydrocarbons over water to provide a first exhaust stream, and flowing the first exhaust gas stream over a catalyst to convert any residual hydrocarbons and other pollutants contained in the first exhaust gas stream to innocuous products and provide a treated exhaust stream and discharging the treated exhaust stream into the atmosphere. The combination of molecular sieves includes SSZ-98 in combination with: (1) a small pore crystalline molecular sieve or mixture of molecular sieves having pores no larger than 8-membered rings selected from the group consisting of SSZ-13, SSZ-16, SSZ-36, SSZ-39, SSZ-50, SSZ-52 and SSZ-73 and having a mote ratio of at least 10 of (a) at least one oxide of at least one tetravalent element to (b) one or more oxides selected from the group consisting of oxides of trivalent elements, pentavalent elements, and mixtures thereof; and/or (2) a large pore crystalline molecular sieve having pores at least as large as 10-membered rings selected from the group consisting of SSZ-26, SSZ-33, SSZ-64, zeolite Beta, CIT-1, CIT-6 and ITQ-4 and having a mole ratio of at least 10 of (a) at least one oxide of at least one tetravalent element to (b) one or more oxides selected from the group consisting of oxides of trivalent elements, pentavalent elements, and mixtures thereof.

The engine exhaust gas stream which is to be treated is flowed over a molecular sieve bed comprising molecular sieve SSZ-98 as a first exhaust stream. The first exhaust stream which is discharged from the molecular sieve bed is now flowed over a catalyst to convert the pollutants contained in the first exhaust stream to innocuous components and provide a treated exhaust stream which is discharged into the atmosphere. It is understood that prior to discharge into the atmosphere, the treated exhaust stream can be flowed through a muffler or other sound reduction apparatus well known in the art.

The catalyst which is used to convert the pollutants to innocuous components is usually referred to in the art as a three-component control catalyst because it can simultaneously oxidize any residual hydrocarbons present in the first exhaust stream to carbon dioxide and water, oxidize any residual carbon monoxide to carbon dioxide and reduce any residual nitric oxide to nitrogen and oxygen. In some cases the catalyst cannot be required to convert nitric oxide to nitrogen and oxygen, e.g., when an alcohol is used as the fuel. In this case the catalyst is called an oxidation catalyst. Because of the relatively low temperature of the engine exhaust stream and the first exhaust stream, this catalyst does not function at a very high efficiency, thereby necessitating the molecular sieve bed.

When the molecular sieve bed reaches a sufficient temperature, typically from 150° C. to 200° C., the pollutants which are adsorbed in the bed begin to desorb and are carried by the first exhaust stream over the catalyst. At this point the catalyst has reached its operating temperature and is therefore capable of fully converting the pollutants to innocuous components.

The adsorbent bed used in this disclosure can be conveniently employed in particulate form or the adsorbent can be deposited onto a solid monolithic carrier. When particulate form is desired, the adsorbent can be formed into shapes such as pills, pellets, granules, rings, spheres, etc. In the employment of a monolithic form, it is usually most convenient to employ the adsorbent as a thin film or coating deposited on an inert carrier material which provides the structural support for the adsorbent. The inert carrier material can be any refractory material such as ceramic or metallic materials. It is desirable that the carrier material be unreactive with the adsorbent and not be degraded by the gas to which it is exposed. Examples of suitable ceramic materials include sillimanite, petalite, cordierite, mullite, zircon, zircon mullite, spondumene, alumina-titanate, etc. Additionally, metallic materials which are within the scope of this disclosure include metals and alloys as disclosed in U.S. Pat. No. 3,920,583 which are oxidation resistant and are otherwise capable of withstanding high temperatures.

The carrier material can best be utilized in any rigid unitary configuration which provides a plurality of pores or channels extending in the direction of gas flow. The configuration can be a honeycomb configuration. The honeycomb structure can be used advantageously in either unitary form, or as an arrangement of multiple modules. The honeycomb structure is usually oriented such that gas flow is generally in the same direction as the cells or channels of the honeycomb structure. For a more detailed discussion of monolithic structures, refer to U.S. Pat. Nos. 3,767,453 and 3,785,998.

The molecular sieve is deposited onto the carrier by any convenient way well known in the art. A desirable method involves preparing a slurry using the molecular sieve and coating the monolithic honeycomb carrier with the slurry. The slurry can be prepared by means known in the art such as combining the appropriate amount of the molecular sieve and a binder with water. This mixture is then blended by using means such as sonication, milling, etc. This slurry is used to coat a monolithic honeycomb by dipping the honeycomb into the slurry, removing the excess slurry by draining or blowing out the channels, and heating to about 100° C. If the desired loading of molecular sieve is not achieved, the above process can be repeated as many times as required to achieve the desired loading.

Instead of depositing the molecular sieve onto a monolithic honeycomb structure, the molecular sieve can be formed into a monolithic honeycomb structure by means known in the art.

The adsorbent can optionally contain one or more catalytic metals dispersed thereon. The metals which can be dispersed on the adsorbent are the noble metals which consist of platinum, palladium, rhodium, ruthenium, and mixtures thereof. The desired noble metal can be deposited onto the adsorbent, which acts as a support, in any suitable manner well known in the art. One example of a method of dispersing the noble metal onto the adsorbent support involves impregnating the adsorbent support with an aqueous solution of a decomposable compound of the desired noble metal or metals, drying the adsorbent which has the noble metal compound dispersed on it and then calcining in air at a temperature of 400° C. to 500° C. for a time of from 1 to 4 hours. By decomposable compound is meant a compound which upon heating in air gives the metal or metal oxide. Examples of the decomposable compounds which can be used are set forth in U.S. Pat. No. 4,791,091. Examples of decomposable compounds are chloroplatinic acid, rhodium trichloride, chloropalladic acid, hexachloroiridate(IV) acid and hexachlororuthenate(IV). It is typical that the noble metal be present in an amount ranging from 0.01 to 4 wt. % of the adsorbent support. Specifically, in the case of platinum and palladium the range is from 0.1 to 4 wt. %, while in the case of rhodium and ruthenium the range is from 0.01 to 2 wt. %.

These catalytic metals are capable of oxidizing the hydrocarbon and carbon monoxide and reducing the nitric oxide components to innocuous products. Accordingly, the adsorbent bed can act both as an adsorbent and as a catalyst.

The catalyst which is used in this disclosure is selected from any three component control or oxidation catalyst well known in the art. Examples of catalysts are those described in U.S. Pat. Nos. 4,528,279; 4,760,044; 4,791,091; 4,868,148; and 4,868,149. Desirable catalysts well known in the art are those that contain platinum and rhodium and optionally palladium, while oxidation catalysts usually do not contain rhodium. Oxidation catalysts usually contain platinum and/or palladium metal. These catalysts can also contain promoters and stabilizers such as barium, cerium, lanthanum, nickel, and iron. The noble metals promoters and stabilizers are usually deposited on a support such as alumina, silica, titania, zirconia, alumino silicates, and mixtures thereof with alumina being desirable. The catalyst can be conveniently employed in particulate form or the catalytic composite can be deposited on a solid monolithic carrier with a monolithic carrier being desirable. The particulate form and monolithic form of the catalyst are prepared as described for the adsorbent above. The molecular sieve used in the adsorbent bed is SSZ-98.

EXAMPLES

The following illustrative examples are intended to be non-limiting.

Example 1

0.74 g of a 45% KOH solution, 4.57 g of deionized water and 0.21 g of a 50% aluminum hydroxide solution (Barcroft™ 0250 aluminum hydroxide, SPI Pharma) were mixed together in a Teflon liner. Then, 1.85 g of a 19% dimethyl DABCO hydroxide solution was added to the mixture. Next, 2.00 g of colloidal silica (LUDOX® AS-40, W.R. Grace & Co.) was added to the mixture and the gel was stirred until it became homogeneous. The liner was then capped and placed within a Parr steel autoclave reactor. The autoclave was placed in an oven and heated at 140° C. for 5 days and then at 180° C. for another 3-4 days. The solid products were recovered from the cooled by centrifugation, washed with deionized water and dried at 95° C.

The resulting product had a $SiO_2/Al_2O_3$ mole ratio of 10.6, as determined by ICP elemental analysis.

Figure 2:
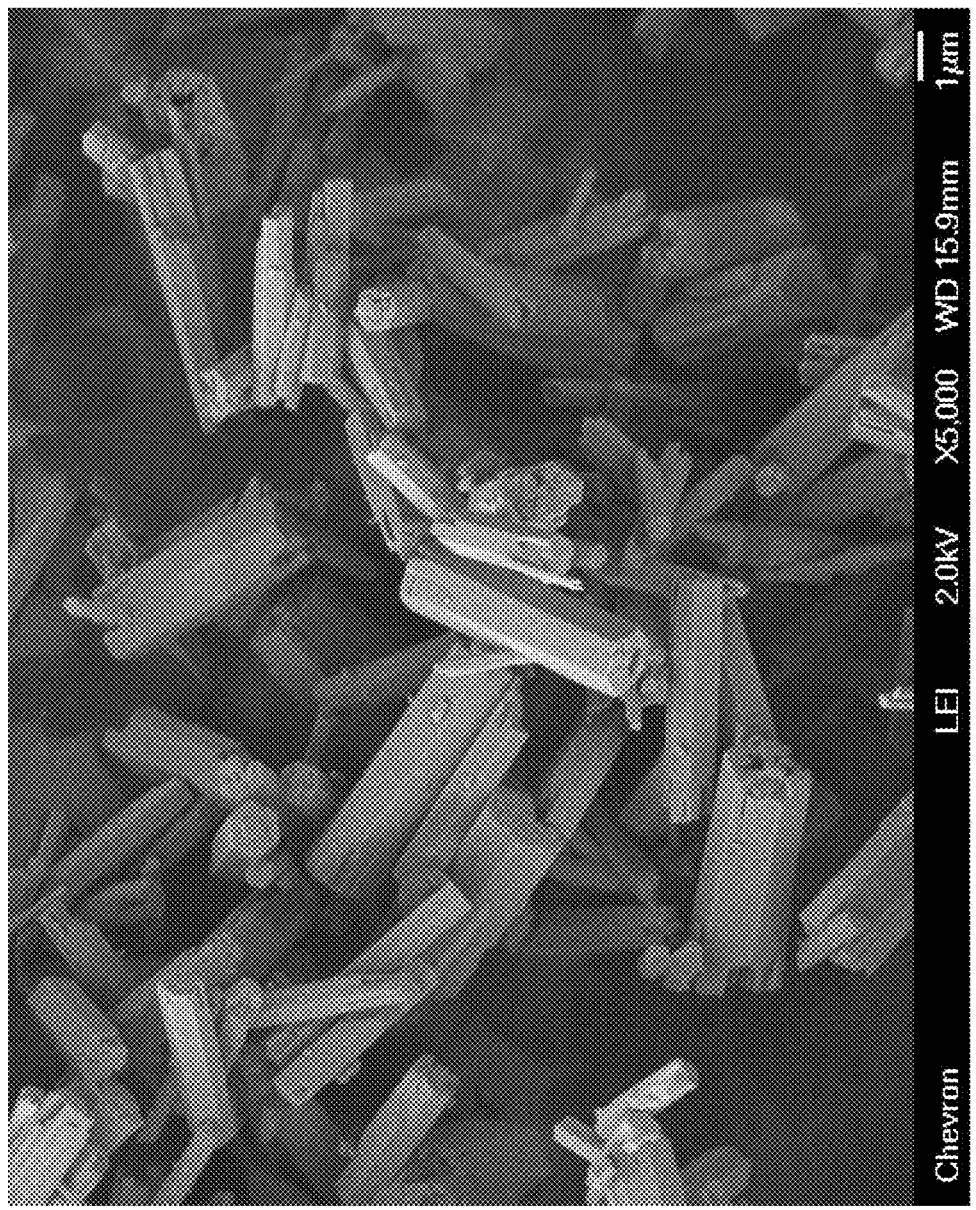
FIG. 2 is a Scanning Electron Microscopy (SEM) image of the as-synthesized molecular sieve prepared in Example 1.

The resulting product was analyzed by powder XRD and SEM. The powder X-ray diffraction pattern for the as-synthesized product is shown in FIG. 1 and indicates that the material is a single phase ERI framework type molecular sieve. SEM image (FIG. 2) for the as-synthesized product shows predominantly rod-like crystal morphology. As used herein, the term "rod-like" refers to a shape which is elongated along one axial direction, and in which the thickness is substantially constant along the longest axis.

Figure 3:
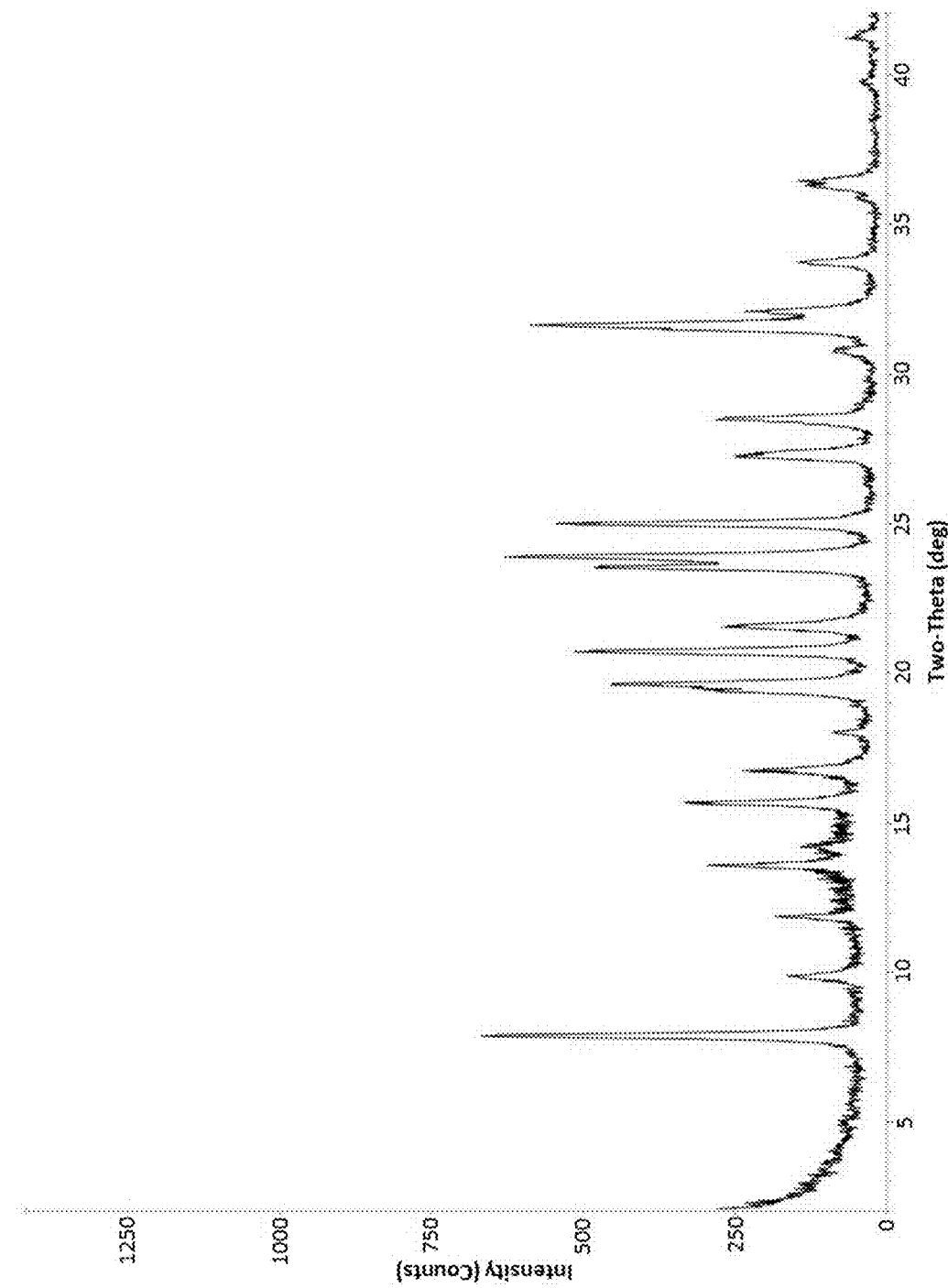
FIG. 3 is a powder XRD pattern of the calcined molecular sieve prepared in Example 1.

The as-synthesized product was then calcined inside a muffle furnace under a flow of air heated to 595° C. at a rate of VC/min and held at 595° C. for five hours. The powder XRD pattern is shown in FIG. 3 and indicates that the material remains stable after calcination to remove the organic SDA.

The calcined product was subjected to a micropore volume analysis using $N_2$ as adsorbate and via the BET method. The measured micropore volume was 0.15 $cm^3/g$. The calcined product after ammonium ion-exchange had a micropore volume of 0.20 $cm^3/g$.

Example 2

1.72 g of a 45% KOH solution, 0.57 g of deionized water and 0.41 g of a 50% aluminum hydroxide solution (Barcroft™ 0250 aluminum hydroxide) were mixed together in a Teflon liner. Then, 9.24 g of a 19% dimethyl DABCO hydroxide solution was added to the mixture. Next, 6.07 g of colloidal silica (LUDOX® AS-40) and 0.38 g of ERI seeds were added to the mixture and the gel was stirred until it became homogeneous. The liner was then capped and placed within a Parr steel autoclave reactor. The autoclave was placed in an oven and heated at 150° C. for 5 days. The solid products were recovered from the cooled by centrifugation, washed with deionized water and dried at 95° C.

The resulting product had a $SiO_2/Al_2O_3$ mole ratio of 17.3, as determined by ICP elemental analysis.

Figure 4:
FIG. 4 is a SEM image of the as-synthesized molecular sieve prepared in Example 2.

The as-synthesized product was analyzed by powder XRD and SEM. The X-ray diffraction pattern showed the product to be a single phase ERI framework type molecular sieve. The SEM image (FIG. 4) for the as-synthesized product shows predominantly a plate crystal morphology. Preferably, the plate crystal morphology is such as the width (W) and the thickness (T) are as follows: W/T is ≥10 and advantageously ranges from 10 to 100.

Example 3

8.17 g of a 45% KOH solution, 10.41 g of deionized water and 10.19 g of LZ-210 (dealuminated Y-molecular sieve with a $SiO_2/Al_2O_3$ mole ratio of 13) were mixed. Then, 30.35 g of a 19% dimethyl DABCO hydroxide solution was added to the mixture. Next, 8.65 g of colloidal silica (LUDOX® AS-40) was added to the mixture and the gel was stirred until it became homogeneous. The solution was then transferred to a Teflon liner and was capped and placed within a Parr steel autoclave reactor. The autoclave was placed in an oven and heated at 150° C. for 6 days. The solid products were recovered from the cooled by centrifugation, washed with deionized water and dried at 95° C.

The resulting product had a $SiO_2/Al_2O_3$ mole ratio of 15.1, as determined by ICP elemental analysis.

Figure 5:
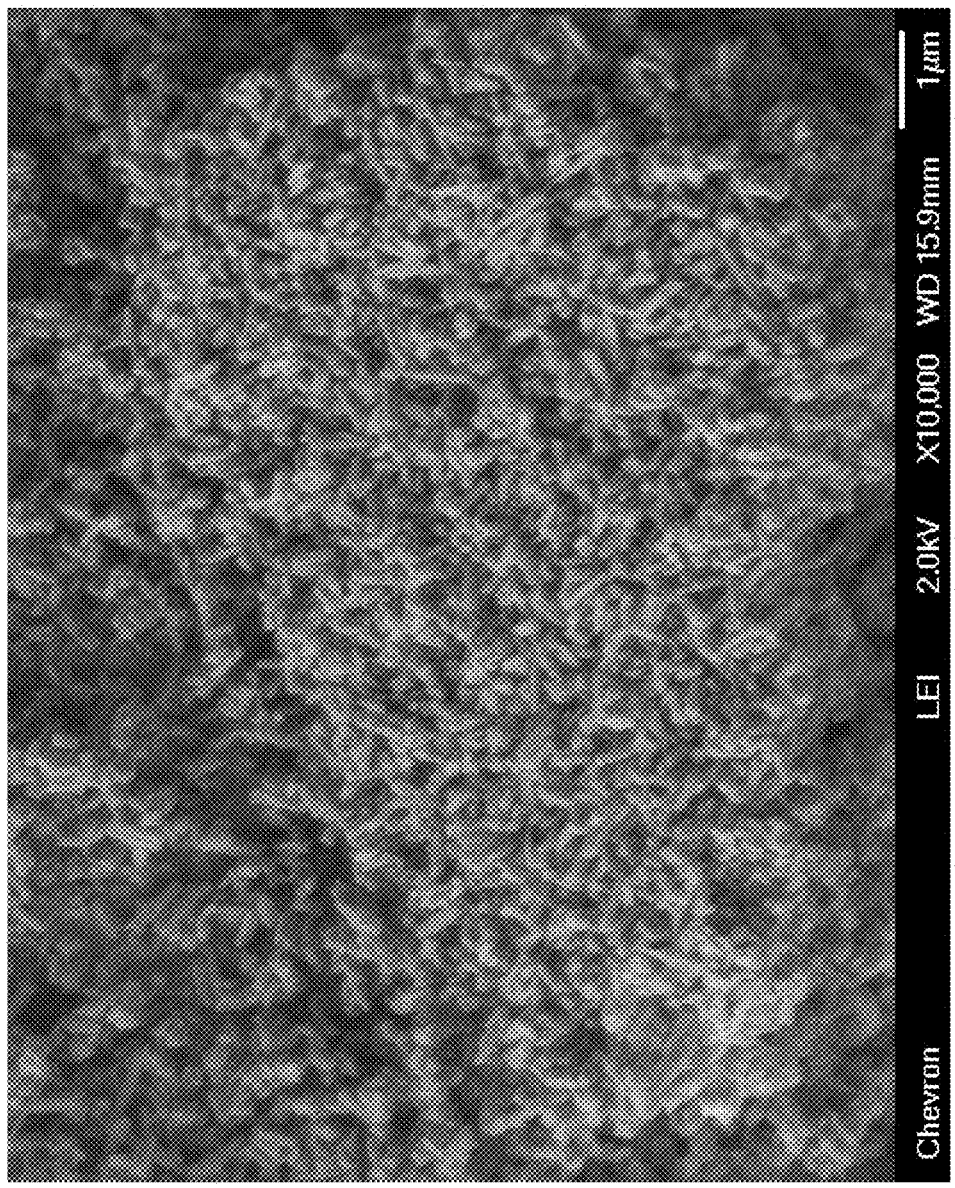
FIG. 5 is a SEM image of the as-synthesized molecular sieve prepared in Example 3.

The reaction product was analyzed by powder XRD and SEM. The X-ray diffraction pattern showed the product to be a single phase ERI framework type molecular sieve. The SEM image (FIG. 5) for the as-synthesized product indicates that the crystal sizes are much smaller than the ones made by Examples 1 and 2.

Example 4

0.82 g of a 45% KOH solution, 2.2 g of deionized water, 1.98 g of a 20% 1,4-dimethyl DABCO hydroxide solution and 1.09 g of CBV 720 (dealuminated Y-molecular sieve with $SiO_2/Al_2O_3$=30, Zeolyst International) were combined in a Teflon liner. The liner was capped and magnetically stirred at room temperature for 3 days. Afterwards, the liner was placed into a stainless steel Parr autoclave and heated at 150° C. for 7 days. The solid products were recovered from the cooled by centrifugation, washed with deionized water and dried at 95° C. The powder X-ray diffraction pattern showed the as-synthesized product to be a single phase ERI framework type molecular sieve.

The product had a $SiO_2/Al_2O_3$ mole ratio of 27.0, as determined by ICP elemental analysis.

Examples 5-21

The procedure of was Example 1 repeated but with the amounts of starting materials being adjusted and/or different Al sources to produce reaction mixtures having the particular mole ratios set forth in Table 5 below. Crystallization was conducted in the same manner as described in Examples 1-4, although in some cases, as shown in Table 5, the crystallization conditions varied somewhat.

Figure 6:
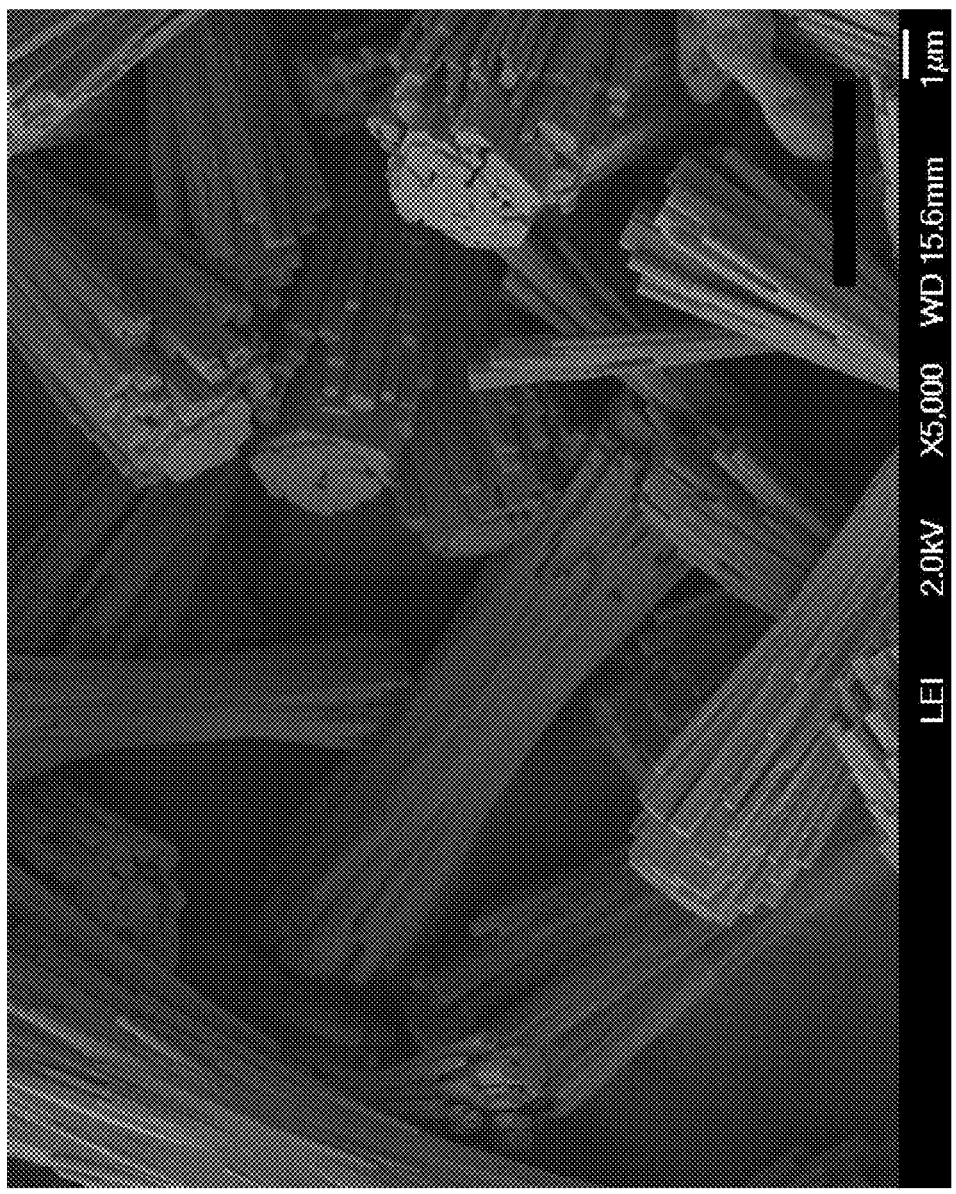
FIG. 6 is a SEM image of the as-synthesized molecular sieve prepared in Example 13.

FIG. 6 is a SEM image of the as-synthesized product of Example 13.

TABLE 5

| Ex. No. | SiO$_2$/Al$_2$O$_3$ | KOH/SiO$_2$ | SrO/SiO$_2$ | Q/SiO$_2$ | A/SiO$_2$ | H$_2$O/SiO$_2$ | ERI Seeds/SiO$_2$ | KFI Seeds/SiO$_2$ | Conditions | Product | Product SiO$_2$/Al$_2$O$_3$ |
|---|---|---|---|---|---|---|---|---|---|---|---|
| 5 | 16.7 | 0.45 | 0 | 0.15 | 0 | 16 | 0 | 0 | 170° C./static/5 d | ERI | 12.3 |
| 6 | 20 | 0.40 | 0 | 0.15 | 0 | 16 | 0.03 | 0 | 150° C./static/6 d | ERI | 16.1 |
| 7 | 20 | 0.40 | 0 | 0.15 | 0 | 16 | 0.03 | 0 | 170° C./static/5 d | ERI | 17.2 |
| 8 | 22.2 | 0.35 | 0 | 0.20 | 0 | 16 | 0.03 | 0 | 150° C./43 rpm rotation/5 d | ERI | 18.5 |
| 9 | 25 | 0.40 | 0 | 0.15 | 0 | 16 | 0.03 | 0 | 150° C./static/6 d | ERI | 20.2 |
| 10 | 28.6 | 0.40 | 0 | 0.15 | 0 | 16 | 0.03 | 0 | 150° C./static/6 d | ERI | 25.0 |
| 11 | 33.4 | 0.40 | 0 | 0.15 | 0.1 | 12 | 0.03 | 0 | 150° C./static/6 d | ERI | 25.7 |
| 12 | 25 | 0.45 | 0 | 0.15 | 0 | 15 | 0 | 0 | 150° C./static/7 d | ERI | 23.0 |
| 13 | 10 | 0.46 | 0.01 | 0.3 | 0.1 | 22 | 0 | 0 | 150° C./static/5 d | ERI | |
| 14 | 10 | 0.46 | 0.01 | 0.3 | 0.1 | 22 | 0 | 0.03 | 150° C./static/5 d | ERI | |
| 15 | 10 | 0.46 | 0 | 0.3 | 0.1 | 22 | 0 | 0 | 150° C./static/5 d | ERI | |
| 16 | 10 | 0.46 | 0 | 0.3 | 0.1 | 22 | 0 | 0.03 | 150° C./static/5 d | ERI | |
| 17 | 20 | 0.46 | 0.01 | 0.3 | 0.1 | 22 | 0 | 0 | 150° C./static/5 d | ERI | |
| 18 | 20 | 0.46 | 0.01 | 0.3 | 0.1 | 22 | 0 | 0.03 | 150° C./static/5 d | ERI | |
| 19 | 10 | 0.46 | 0 | 0.2 | 0.1 | 22 | 0 | 0.03 | 150° C./static/5 d | ERI | |
| 20 | 40 | 045 | 0 | 0.15 | 0 | 16 | 0 | 0 | 150° C./43 rpm rotation/7 d | ERI | 19 |
| 21 | 40 | 0.45 | 0 | 0.15 | 0 | 15 | 0 | 0 | 150° C./43 rpm rotation/7 d | ERI | 14 |

Q = N,N'-dimethyl-1,4-diazabicyclo[2.2.2]octane dication
A = 18-crown-6

Example 22

Methanol Conversion

Ammonium-exchanged SSZ-98 was pelletized at 5 kpsi, crushed and meshed to 20-40. 0.20 g of catalyst (diluted 4:1 v/v with alundum) was centered in a stainless steel down-flow reactor in a split tube furnace. The catalyst was pre-heated in-situ under flowing nitrogen at 400° C. A feed of 10% methanol in nitrogen was introduced into the reactor at a rate of 1.3 h$^{-1}$ WHSV.

Reaction data was collected using a plug flow and an Agilent on-line gas chromatograph with an FID detector. Reaction products were analyzed at 1 hour and 2 hours on an HP-PLOT Q column. The results are summarized in Table 6.

TABLE 6

| Product | 1 Hour Data | 2 Hour Data | 3 Hour Data | 4 Hour Data |
|---|---|---|---|---|
| Conversion | 1.00 | 1.00 | 1.00 | 1.00 |
| Sum C$_1$-C$_3$ paraffin | 0.12 | 0.09 | 0.07 | 0.08 |
| Ethylene | 0.43 | 0.54 | 0.61 | 0.72 |
| Propylene | 0.24 | 0.20 | 0.21 | 0.16 |
| Summed Butanes/Butenes | 0.16 | 0.12 | 0.07 | 0.08 |
| Summed Pentanes/Pentenes | 0.05 | 0.05 | 0.04 | 0.01 |
| Ethylene/Propylene ratio | 1.83 | 2.75 | 2.87 | 4.45 |

The products shown in Table 6 are consistent with those for a small pore zeolite in terms of product shape-selectivity in the reaction of methanol being catalytically converted to olefins of mostly C$_2$-C$_4$ size. No aromatic products were observed.

Example 23

NO$_x$ Conversion

Calcined SSZ-98 loaded with copper by weight via an incipient wetness process. The ion-exchanged material was then activated by increasing the temperature of the material from room temperature to 150° C. at a rate of 2° C./minute, holding the material at 150° C. for 16 hours, then increasing the temperature of the material to 450° C. at a rate of 5° C./minute, holding the material at 450° C. for 16 hours. The material was then allowed to cool to room temperature again.

Fresh (i.e., un-aged) and aged (i.e., at 750° C. for 24 hours in a 10% H$_2$O in air gas mixture) Cu-SSZ-98 material was tested using a Synthetic Catalyst Activity Test (SCAT) rig under the following conditions: 500 ppm NO, 500 ppm NH$_3$, 10% O$_2$, 10% H$_2$O and the balance N$_2$; and a space velocity of 60,000/hour.

For comparison, a reference ERI framework type material was also tested. The comparative sample was loaded with a similar amount of copper, underwent similar hydrothermal aging, and was tested using the SCAT rig under similar conditions.

Figure 7:
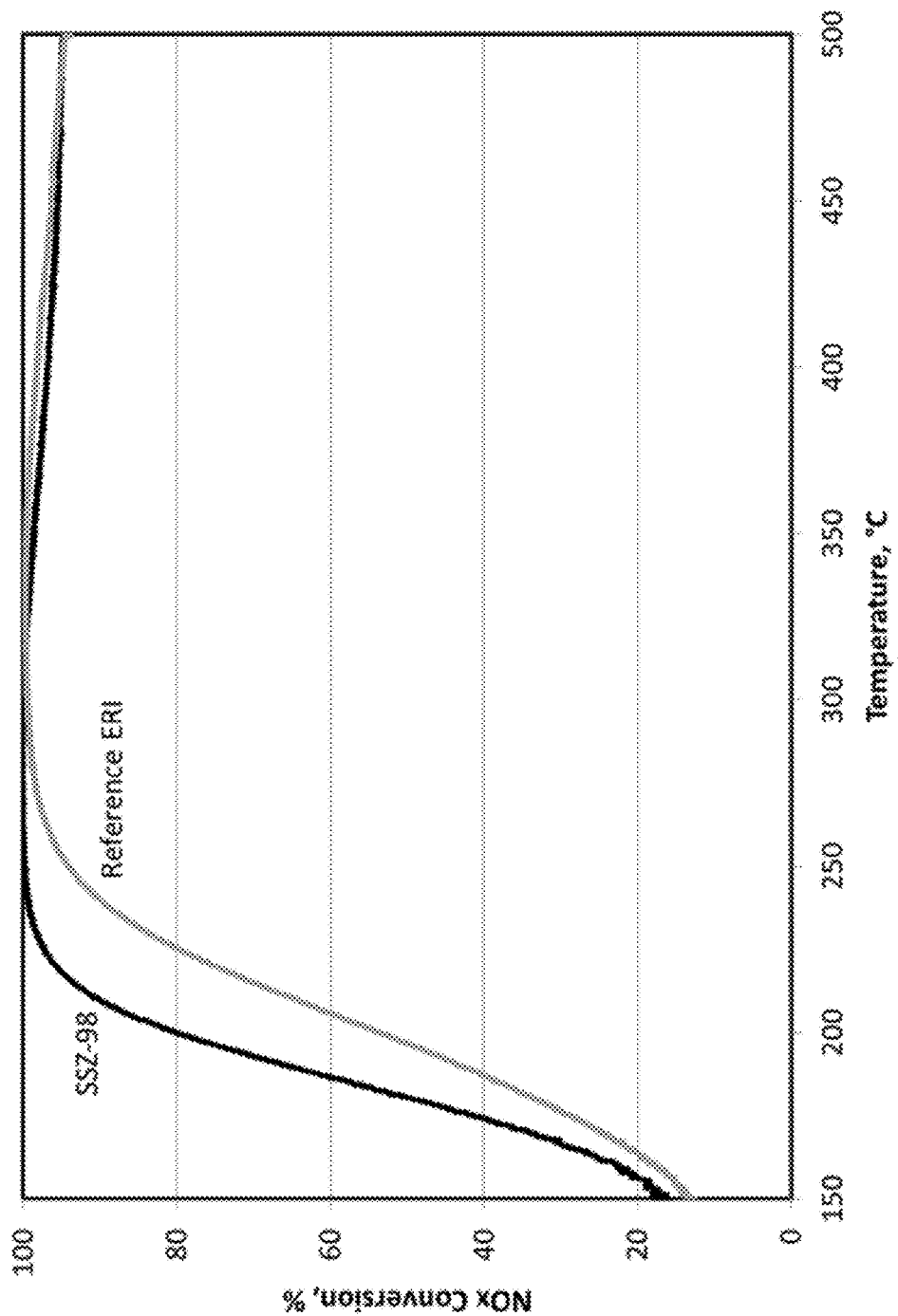
FIG. 7 is a graph comparing the $NO_x$ conversion activity of (1) fresh SSZ-98 catalyst and (2) fresh reference ERI catalyst.
Figure 8:
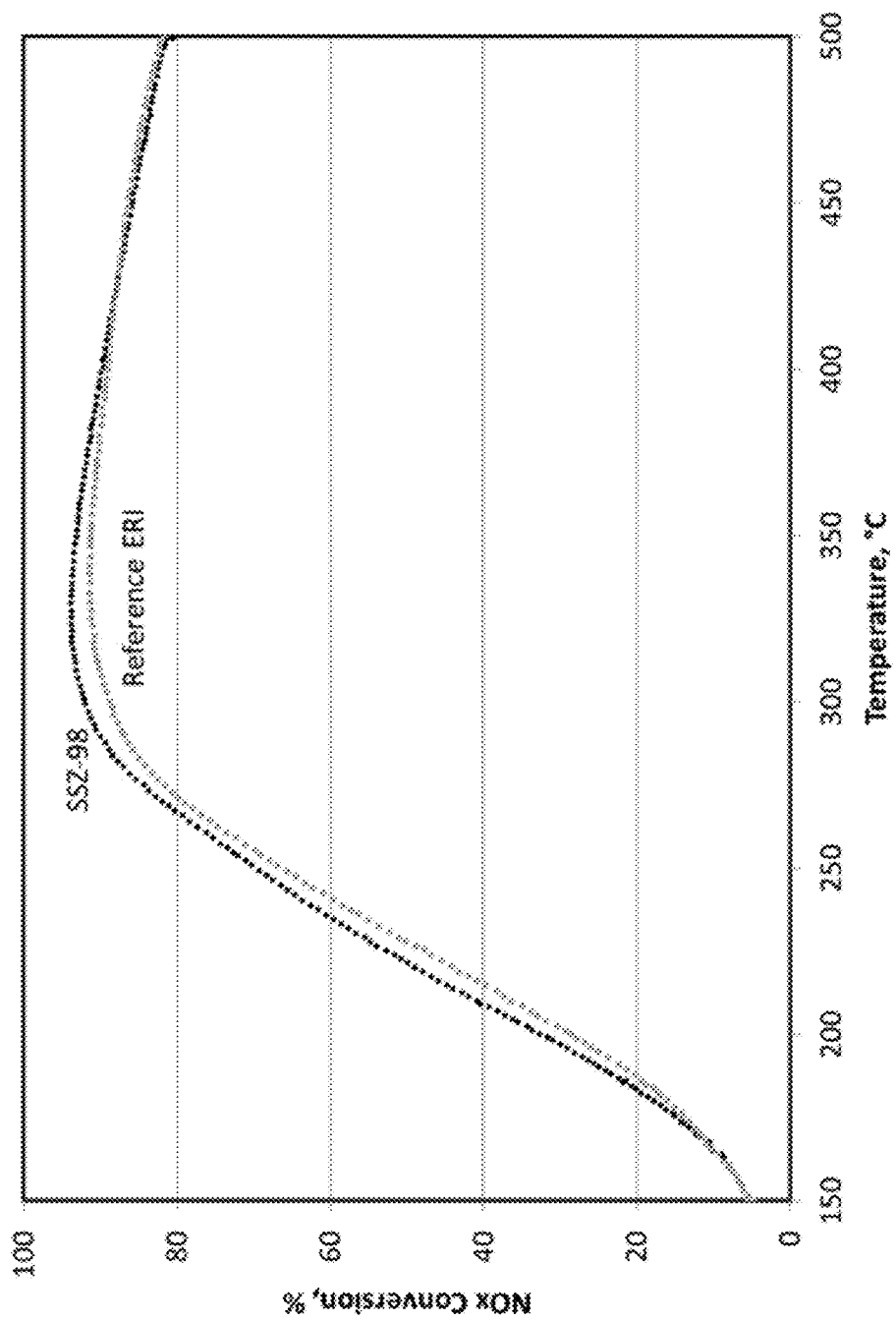
FIG. 8 is a graph comparing the $NO_x$ conversion activity of (1) aged SSZ-98 catalyst and (2) aged reference ERI catalyst.

The samples were tested to determine NO$_x$ conversion (e.g., into N$_2$ and O$_2$) as a function of temperature. FIG. 7 is a graph comparing the NO$_x$ conversion activity of (1) fresh SSZ-98 catalyst and (2) fresh reference ERI catalyst. FIG. 8 is a graph comparing the NO conversion activity of (1) aged SSZ-98 catalyst and (2) aged reference ERI catalyst. As is evident from FIG. 8 and FIG. 9, the SSZ-98 catalysts demonstrate enhanced NO$_x$ conversion efficiencies comparable to and/or better than the reference ERI catalysts.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. In a process for separating gases using a membrane containing a molecular sieve, the improvement comprising using as the molecular sieve an ERI framework type molecular sieve having a $SiO_2/Al_2O_3$ mole ratio of from 15 to 50, and having, in its calcined form, an X-ray diffraction substantially as shown in the following Table:

| 2-Theta | d-spacing (nm) | Relative Intensity |
|---|---|---|
| 7.76 ± 0.20 | 1.138 | VS |
| 9.78 ± 0.20 | 0.904 | W |
| 11.79 ± 0.20 | 0.750 | W |
| 13.45 ± 0.20 | 0.658 | VS |
| 14.07 ± 0.20 | 0.629 | W |
| 15.51 ± 0.20 | 0.571 | W |
| 16.61 ± 0.20 | 0.533 | W |
| 19.50 ± 0.20 | 0.455 | W |
| 20.54 ± 0.20 | 0.432 | S |
| 21.39 ± 0.20 | 0.415 | W |
| 23.37 ± 0.20 | 0.380 | M |
| 23.73 ± 0.20 | 0.375 | S |
| 24.92 ± 0.20 | 0.357 | W | and wherein the molecular sieve has either a rod-like crystal morphology or a plate crystal morphology.

2. A process for the production of light olefins from a feedstock comprising an oxygenate or mixture of oxygenates, the process comprising reacting the feedstock at effective conditions over a catalyst comprising an ERI framework type molecular sieve having a $SiO_2/Al_2O_3$ mole ratio of from 15 to 50, and having, in its calcined form, an X-ray diffraction pattern substantially as shown in the following Table:

| 2-Theta | d-spacing (nm) | Relative Intensity |
|---|---|---|
| 7.76 ± 0.20 | 1.138 | VS |
| 9.78 ± 0.20 | 0.904 | W |
| 11.79 ± 0.20 | 0.750 | W |
| 13.45 ± 0.20 | 0.658 | VS |
| 14.07 ± 0.20 | 0.629 | W |
| 15.51 ± 0.20 | 0.571 | W |
| 16.61 ± 0.20 | 0.533 | W |
| 19.50 ± 0.20 | 0.455 | W |
| 20.54 ± 0.20 | 0.432 | S |
| 21.39 ± 0.20 | 0.415 | W |
| 23.37 ± 0.20 | 0.380 | M |
| 23.73 ± 0.20 | 0.375 | S |
| 24.92 ± 0.20 | 0.357 | W | and wherein the molecular sieve has either a rod-like crystal morphology or a plate crystal morphology.

3. The process of claim 2, wherein the light olefins are ethylene, propylene, butylene, or mixtures thereof.

4. The process of claim 2, wherein the oxygenate is methanol, dimethyl ether, or a mixture thereof.

5. A process for producing methylamine or dimethylamine comprising reacting methanol, dimethyl ether, or a mixture thereof, and ammonia in the gaseous phase in the presence of a catalyst comprising an ERI framework type molecular sieve having a $SiO_2/Al_2O_3$ mole ratio of from 15 to 50, and having, in its calcined form, an X-ray diffraction pattern substantially as shown in the following Table:

| 2-Theta | d-spacing (nm) | Relative Intensity |
|---|---|---|
| 7.76 ± 0.20 | 1.138 | VS |
| 9.78 ± 0.20 | 0.904 | W |
| 11.79 ± 0.20 | 0.750 | W |
| 13.45 ± 0.20 | 0.658 | VS |
| 14.07 ± 0.20 | 0.629 | W |
| 15.51 ± 0.20 | 0.571 | W |
| 16.61 ± 0.20 | 0.533 | W |
| 19.50 ± 0.20 | 0.455 | W |
| 20.54 ± 0.20 | 0.432 | S |
| 21.39 ± 0.20 | 0.415 | W |
| 23.37 ± 0.20 | 0.380 | M |
| 23.73 ± 0.20 | 0.375 | S |
| 24.92 ± 0.20 | 0.357 | W | and wherein the molecular sieve has either a rod-like crystal morphology or a plate crystal morphology.

6. A process for the reduction of oxides of nitrogen contained in a gas stream wherein the process comprises contacting the gas stream with an ERI framework type molecular sieve having a $SiO_2/Al_2O_3$ mole ratio of from 15 to 50, and having, in its calcined form, an X-ray diffraction pattern substantially as shown in the following Table:

| 2-Theta | d-spacing (nm) | Relative Intensity |
|---|---|---|
| 7.76 ± 0.20 | 1.138 | VS |
| 9.78 ± 0.20 | 0.904 | W |
| 11.79 ± 0.20 | 0.750 | W |
| 13.45 ± 0.20 | 0.658 | VS |
| 14.07 ± 0.20 | 0.629 | W |
| 15.51 ± 0.20 | 0.571 | W |
| 16.61 ± 0.20 | 0.533 | W |
| 19.50 ± 0.20 | 0.455 | W |
| 20.54 ± 0.20 | 0.432 | S |
| 21.39 ± 0.20 | 0.415 | W |
| 23.37 ± 0.20 | 0.380 | M |
| 23.73 ± 0.20 | 0.375 | S |
| 24.92 ± 0.20 | 0.357 | W | and wherein the molecular sieve has either a rod-like crystal morphology or a plate crystal morphology.

7. The process of claim 6, wherein the molecular sieve contains a metal or metal ions capable of catalyzing the reduction of the oxides of nitrogen.

8. The process of claim 7, wherein the metal is lanthanum, chromium, manganese, iron, cobalt, rhodium, nickel, palladium, platinum, copper, zinc, or mixtures thereof.

9. The process of claim 6, wherein the gas stream is the exhaust stream of an internal combustion engine.

10. A process for treating a cold-start engine exhaust gas stream containing hydrocarbons and other pollutants consisting of flowing the engine exhaust gas stream over a molecular sieve bed which preferentially adsorbs the hydrocarbons over water to provide a first exhaust stream, and flowing the first exhaust gas stream over a catalyst to convert any residual hydrocarbons and other pollutants contained in the first exhaust gas stream to innocuous products and provide a treated exhaust stream and discharging the treated exhaust stream into the atmosphere, the molecular sieve bed comprising an ERI framework type molecular sieve having a $SiO_2/Al_2O_3$ mole ratio of from 15 to 50, and having, in its calcined form, an X-ray diffraction pattern substantially as shown in the following Table:

| 2-Theta | d-spacing (nm) | Relative Intensity |
|---|---|---|
| 7.76 ± 0.20 | 1.138 | VS |
| 9.78 ± 0.20 | 0.904 | W |
| 11.79 ± 0.20 | 0.750 | W |
| 13.45 ± 0.20 | 0.658 | VS |
| 14.07 ± 0.20 | 0.629 | W |
| 15.51 ± 0.20 | 0.571 | W |
| 16.61 ± 0.20 | 0.533 | W |
| 19.50 ± 0.20 | 0.455 | W |
| 20.54 ± 0.20 | 0.432 | S |
| 21.39 ± 0.20 | 0.415 | W |
| 23.37 ± 0.20 | 0.380 | M |
| 23.73 ± 0.20 | 0.375 | S |
| 24.92 ± 0.20 | 0.357 | W | and wherein the molecular sieve has either a rod-like crystal morphology or a plate crystal morphology.

11. The process of claim 10, wherein the engine is an internal combustion engine.

12. The process of claim 11, wherein the internal combustion engine is an automobile engine.

13. The process of claim 10, wherein the engine is fueled by a hydrocarbon fuel.

14. The process of claim 10, wherein the molecular sieve has deposited on it a metal selected from the group consisting of ruthenium, rhodium, palladium, platinum, and mixtures thereof.

15. The process of claim 14, wherein the metal is palladium, platinum, or a mixture thereof.

* * * * *